US007727965B2

(12) United States Patent
Wang et al.

(10) Patent No.: US 7,727,965 B2
(45) Date of Patent: Jun. 1, 2010

(54) C-GLYCOSYLISOFLAVONES HAVING ALKYLAMINOALKOXYL SUBSTITUENT, PREPARATION AND USE OF THE SAME

(75) Inventors: Lin Wang, Beijing (CN); Qiujun Lu, Beijing (CN); Shengqi Wang, Beijing (CN); Tao Peng, Beijing (CN); Xiaowei Zhu, Beijing (CN); Shouguo Zhang, Beijing (CN); Jianping Ren, Beijing (CN); Lu Li, Beijing (CN); Ling Han, Beijing (CN); Yiguang Jin, Beijing (CN); Fengsheng Che, Hainan (CN)

(73) Assignees: Hainan Yangpu New & Special Medicine Co., Ltd., Hainan (CN); Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 416 days.

(21) Appl. No.: 10/563,471

(22) PCT Filed: Jul. 2, 2004

(86) PCT No.: PCT/CN2004/000728

§ 371 (c)(1),
(2), (4) Date: Mar. 14, 2008

(87) PCT Pub. No.: WO2005/003146

PCT Pub. Date: Jan. 13, 2005

(65) Prior Publication Data

US 2008/0293642 A1 Nov. 27, 2008

(30) Foreign Application Priority Data

Jul. 3, 2003 (CN) ............... 03 1 48547

(51) Int. Cl.
*A01N 43/04* (2006.01)
*C07H 1/00* (2006.01)
*C07H 7/06* (2006.01)

(52) U.S. Cl. ............ 514/23; 536/1.11; 536/29.2; 536/124

(58) Field of Classification Search .......... None
See application file for complete search history.

(56) References Cited

FOREIGN PATENT DOCUMENTS

CN 1394603 A 2/2003
WO WO2004/002470 1/2004

OTHER PUBLICATIONS

Gao et al. (Synthesis of Daidzin Analogues as Potential Agents for Alcohol Abuse), Bioorganic & Medicinal Chemistry, 2003, 4069-81, 11 (18).*
Yang Ruolin, et al., "Preparation and Bio-activity of Puerarin Derivatives", Journal of China Pharmaceutical University, 1999, vol. 30, No. 2, pp. 81-85, with English abstract (last page).
Hou, et al., "Study on the preparation of 7,4'-di-O-hydroxyethyl puerarin", Chinese Journal of Medicinal Chemistry, Apr. 2002, vol. 12, No. 2, pp. 103-104, with English abstract (last page).
Guang-Yao Gao, et al., "Synthesis of Daidzin Analogues as Potential Agents for Alcohol Abuse," Bioorganic & Medicinal Chemistry, 2003, vol. 11, pp. 4069-4081.
Wang Jing, et al., "Study Achievement of Puerarin," 2003, vol. 27, No. 2, pp. 70-73, with English abstract.
Cheng Weijin, et al., "Survey on the Fever Caused by Kakonein Injection" 1995-2006 Tsinghua Tongfang Optical Disc Co., Ltd., 2000, 9(3); pp. 129-130, with English abstract.
Wu Zhenghong, et al., "Studies on the Solubility of Puerarin and the Solubilizing Effect of Polymer," Tsinghua Tongfang Optical Disc Co., Ltd. (1995-2006) 1999, 7(1); pp. 10-11.
International Search Report dated Sep. 30, 2004 of corresponding PCT/CN2004/000728.

* cited by examiner

*Primary Examiner*—Traviss C McIntosh, III
(74) *Attorney, Agent, or Firm*—Christie, Parker & Hale, LLP

(57) ABSTRACT

The present invention relates to C-Glycosylisoflavones having alkylaminoalkoxyl substituent and pharmaceutically acceptable salts thereof, a process for the preparation thereof, pharmaceutical compositions comprising an effective amount of a compound of the formula (I), and to the use of these compounds or compositions for the treatment or prevention of cardio- and cerebrovascular diseases, in particular for the treatment of various cardiocerebral hypoxic-ischemic diseases, for the treatment or prevention of diabetes mellitus and complications thereof, and for the treatment or prevention of chemical poisoning, in particular alcoholism.

10 Claims, No Drawings

C-GLYCOSYLISOFLAVONES HAVING ALKYLAMINOALKOXYL SUBSTITUENT, PREPARATION AND USE OF THE SAME

CROSS-REFERENCE TO RELATED APPLICATION

This application is a National Phase patent application of International Application Number PCT/CN2004/000728, filed on Jul. 2, 2004, which claims priority of Chinese Patent Application Number 03148547.2, filed on Jul. 3, 2003.

TECHNICAL FIELD

The present invention relates to C-Glycosylisoflavones having alkylaminoalkoxyl substituent and pharmaceutically acceptable salts thereof, a process for the preparation thereof, pharmaceutical compositions comprising an effective amount of a compound of the formula (I), and to the use of these compounds or compositions for the treatment or prevention of cardio- and cerebrovascular diseases, in particular for the treatment of various cardiocerebral hypoxic-ischemic diseases, for the treatment or prevention of diabetes mellitus and complications thereof, and for the treatment or prevention of chemical poisoning, in particular alcoholism.

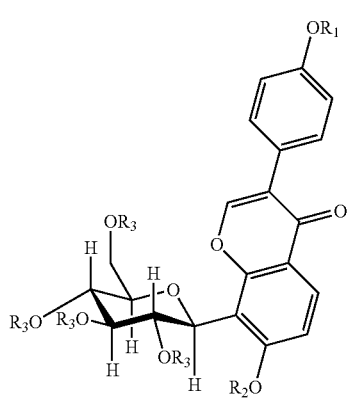

(I)

BACKGROUND ARTS

Puerarin (formula (I), wherein $R_1=R_2=R_3=H$) is an effective ingredient in Kudzuvine Root (Radix Puerariae), a leguminous plant, and has a chemical name of 4',7-dihydroxy-8-β-D-C-glycosylisoflavone. In the recent decades, the mechanism and applications of puerarin are studied, and it is proven that puerarin does have effects such as expanding coronary artery, improving cardiac contractility, protection global ischemia cardiac muscle, promoting blood circulation, etc. At present, puerarin is widely used clinically for the treatment of coronary heart disease, angina pectoris, myocardial infarct, arrhythmia, cardiac failure, vertebro-basilar artery insufficiency, hyperviscosity syndrome, hypertension, cerebral thrombosis, cerebral edema, retinal arterial obstruction, retinal vein obstruction, sudden deafness, diabetes and complications thereof, pesticide intoxication, alcoholism, and tumors, etc. (Wang Jing, Ji Min, Hua Weiyi, et al., Study Achievement of Puerarin, *Yaoxue Xuebao* (*Acta Pharmaceutica Sinica*), 2003, 27(2):70-3). At present, cardio- and cerebrovascular diseases are the primary diseases causing adult death in China. Being a new drug for improving cardio- and cerebrovascular blood circulation, puerarin has a novel structure and definite therapeutic effects, and thus is important for the treatment of these diseases.

It has been reported in the prior arts that puerarin has some adverse effects in clinical applications, which mainly manifest in febrile, allergies, drug eruptions, transient hemoglobinuria, etc. Cheng Weijin, et al. (*Yaowu Liuxingbing Zazhi* (*Chinese Journal of Pharmacoepidemiology*), 2000, 9(3):129-130) had made an investigation on 568 patients who had administered with puerarin, and the results indicates that the total incidence rate of febrile was 5.81%, there was no significant difference in age and gender and in dosage, and the febrile mainly related to the days of sustained medication. The patients' body temperature gradually decreased to normal level after drug withdrawal or the patients were treated by antipyresis simultaneously. The treatment with antibiotics was ineffective. This might be caused by the toxic effect of drug accumulation during the long time of therapy; and the drug might penetrate the blood brain barrier, directly stimulate the center of thermoregulation in hypothalamus, affect the procedure of human body heat production and loss, and cause delayed allergy.

A series of simple alkyl esteric and etheric derivatives of puerarin had been synthesized via the modification of phenolic hydroxyl group and alditolic hydroxyl groups and their effects on blood flow of rabbit ocular tissue (Yang Ruolin, Li Na, et al., *Zhongguo Yaoke Daxue Xuebao* (*Journal of China Pharmaceutical University*), 1999, 30(2):81-85; Hou Dianjie, Wang Jianwu, Sun Jianlong, *Zhongguo Yaowu Huaxue Xuebao* (*Chinese Journal of Medicinal Chemistry*), 2002, 12(2):103-4). However, the pharmacodynamic actions and toxicities of these compounds on cardio- and cerebrovascular diseases, diabetes and alcoholism are not studied deeply.

In the prior arts, it is also disclosed that puerarin has poor water-solubility and lipo-solubility, and the solubility of puerarin in water is 0.462 g/100 ml. Solubilizers should be added during the preparations, and common solubilizers are propylene glycol, polyvinylpyrrolidone (PVP), etc. The solubility of puerarin in 4.3% PVP aqueous solution is 1.332 g/100 ml. The solubility of puerarin also depends on pH value, and puerarin in an aqueous solution has a poor stability at a relatively high pH value. The pH generally should be controlled at 6.5 or lower during the complexing and dissolving procedure (Wu Zhenghong, Zhu Yanqin, et al., *Jiangsu Yaoxue Yu Linchuang Yanjiu* (*Jiangsu Pharmaceutical and Clinical Researches*), 1999, 7(1): 9-12).

The prior art further discloses that puerarin has a relatively low oral bioavailability of about 30%, and is administered by intravenous injection in clinic. The poor water-solubility, oral bioavailability and adverse effects of puerarin render the value of puerarin as pharmaceuticals.

So far, no document has been found that relates to the puerarin-based compounds of the present invention, i.e., C-Glycosylisoflavones having alkylaminoalkoxyl substituent, and to the use of these compounds for the treatment and prevention of cardio- and cerebrovascular disease, diabetes, and chemical poisoning.

SUMMARY OF THE INVENTION

One object of the present invention is to provide C-Glycosylisoflavones having alkylaminoalkoxyl substituent in order to overcome the drawbacks in the prior arts.

Another object of the present invention is to provide a process for the preparation of the C-Glycosylisoflavones having alkylaminoalkoxyl substituents.

Yet another object of the present invention is to provide a pharmaceutical composition comprising one or more such compounds.

A further object of the present invention is to provide a use of said compounds in a medicament for treatment and prevention of diseases associated with cardio- and cerebrovascular diseases, in particular hypoxic-ischemic diseases.

One another object of the present invention is to provide a use of said compounds in a medicament for the treatment and prevention of diabetes and complications thereof.

Yet further object of the present invention is to provide a use of said compounds in a medicament for the treatment and prevention of chemical poisoning, in particular alcoholism.

For achieving the objects of the present invention, the present invention employs the following technical solutions:

The present invention relates to a novel alkylaminoalkoxyl-substituted C-Glycosylisoflavone or a pharmaceutically acceptable salt thereof:

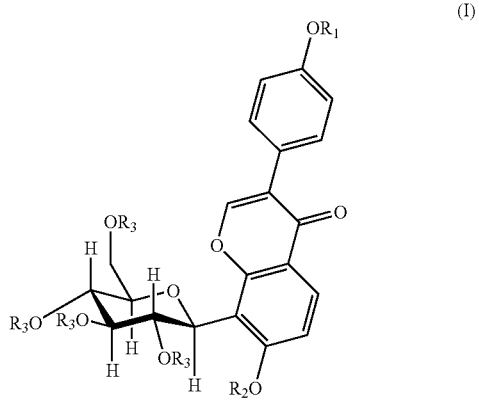

(I)

wherein, $R_1$ and $R_2$ are independently selected from hydrogen, ($C_1$-$C_{12}$) linear, or branched alkylamino, mono- or di-($C_{3-8}$)cycloalkylamino-$C_{1-6}$alkyl, or ($C_5$-$C_{14}$) heterocyclic-($C_1$-$C_6$)alkyl; $R_3$ is selected from hydrogen, ($C_1$-$C_{12}$) linear or branched acyl, or $C_{6-14}$ aryl carbonyl; wherein $R_1$ and $R_2$ do not simultaneously represent hydrogen; the 1-position of the D-glucosyl is connected with the 8-position of the isoflavone in a form of β-configured C-glycoside.

According to the compound of formula (I) of the present invention the substituents are further preferably defined, wherein $R_1$ and $R_2$ are independently selected from hydrogen, dimethylaminoethyl, diethylaminoethyl, di(n-propyl)aminoethyl, di(iso-propyl)aminoethyl, di(n-butyl)aminoethyl, di(iso-butyl)aminoethyl, di(tert-butyl)aminoethyl, pyrrolidinylethyl, piperidylethyl, morpholinylethyl, piperazinylethyl, N-methylpiperazinylethyl, N-ethylpiperazinylethyl, tert-butylaminoethyl, dicyclohexylaminoethyl, dimethylaminopropyl, diethylaminopropyl, di(n-propyl)aminopropyl, di(iso-propyl)aminopropyl, di(n-butyl)aminopropyl, di(iso-butyl)aminopropyl, di-(tert-butyl)aminopropyl, pyrrolidinylpropyl, piperidylpropyl, morpholinylpropyl, piperazinylpropyl, N-methylpiperazinylpropyl, N-ethylpiperazinylpropyl, tert-butylaminopropyl, dicyclohexylaminopropyl; dimethylaminobutyl, diethylaminobutyl, di(n-propyl)aminobutyl, di(iso-propyl)aminobutyl, di(n-butyl)aminobutyl, di(iso-butyl)aminobutyl, di(tert-butyl)aminobutyl, pyrrolidinylbutyl, piperidylbutyl, morpholinylbutyl, piperazinylbutyl, N-methylpiperazinylbutyl, N-ethylpiperazinylbutyl, tert-butylaminobutyl, dicyclohexylaminobutyl; $R_1$ and $R_2$ do not simultaneously represent hydrogen; $R_3$ is selected from hydrogen, propionyl, butyryl, isobutyryl, 2-methylbutyryl, 3-methylbutyryl, 2,2-dimethylpropionyl, valeryl, caproyl, heptanoyl, octanoyl, nonanoyl, decanoyl, lauroyl. The pharmaceutically acceptable salts are selected from salts of various pharmaceutically acceptable organic acids and inorganic acids comprising hydrochloric acid, hydrobromic acid, phosphoric acid, phosphorous acid, sulfuric acid, methane sulfonic acid, p-toluene sulfonic acid, maleic acid, fumaric acid, tartaric acid, and various natural or non-natural amino acids.

The process of the present invention for preparing the compounds of formula (I) comprises: reacting puerarin as raw material with a suitable bifunctional compound at a room- to reflux-temperature in a suitable solvent under the presense of a base, which is firstly mono-etherified followed by amination. Specifically, the suitable bifunctional compound includes bihalogenated hydrocarbons, alkylene bissulfonates, and halogenated hydrocarbon monosulfonates, such as 1,2-dichloroethane, 1,2-dibromoethane, 1,2-diiodoethane, 1,2-dichloropropane, 1,2-dibromopropane, 1,2-diiodopropane, 1,3-dichloropropane, 1,3-bromopropane, 1,3-diiodopropane, 1,2-dichlorobutane, 1,2-dibromobutane, 1,2-diiodobutane, 1,4-dichlorobutane, 1,4-dibromobutane, 1,4-diiodobutane, 1,2-ethylenedissulfonate, 1,2-propylene dissulfonate, 1,3-propylenedissulfonate, 1,2-butylenedissulfonate, 1,3-butylene dissulfonate, and 1,4-butylene dissulfonate, etc. The solvent includes water, acetone, dimethylformamide, dimethyl sulfoxide, and lower alcohols, wherein the lower alcohol is selected from methanol, ethanol, propanol, isopropanol, butanol, isobutanol, tert-butanol, pentanol, 2,2-dimethyl-propan-1-ol, pentan-2-ol, pentan-3-ol and hexanol, etc.

The further preferred compounds of the present invention are pharmaceutical salts of the compounds of formula (I), such as hydrochlorides, and these preferred compounds have better solubility in water at normal temperature than that of puerarin.

The present invention further relates to a pharmaceutical composition comprising a pharmaceutically effective amount of a compound of formula (I) and a pharmaceutically acceptable carrier.

The pharmacological studies indicated that the compounds of formula (I) have effects of vasodilatation, can significantly prolong the time to death caused by hypoxia in mice, and show protection effects on ex vivo cardiac postischemic reperfusion damage in rats. The compounds of the present invention have effects of vasodilatation, which have coronary artery and cerebral vessel dilation effect, reduction of myocardial consumption of oxygen, microcirculation improvement and antiplatelet effects, and have potential effects for the prevention of cardiocerebral hypoxia-ischemia.

The compounds of the present invention are novel compounds having the skeleton of puerarin, and can be used for the prevention and treatment of coronary artery diseases, various angina pectoris attacks, myocardial infarcts, cerebrovascular diseases, diabetes and complications thereof, and chemical poisoning, in particular alcoholism.

The pharmaceutical composition comprising an effective amount of the compound of the present invention can be prepared via utilizing common known pharmaceutically acceptable carriers in the art.

The compounds of the present invention or compositions thereof can be administered orally or parenterally. Oral formulations may be tablets, capsules and coated drugs, and parenteral formulations may be injections and suppositories, etc. These preparations can be prepared via utilizing common known methods familiar to those skilled in the art. To prepare tablets, capsules and coated drugs, the accessories may be conventional accessories, such as starch, gelatin, Arabia gum, silica, polyethylene glycol; solvents for liquid preparations may be, such as water, ethanol, propylene glycol; vegetable oils may be, such as corn oil, peanut oil, olive oil, etc. The preparations comprising the compounds of the present invention may further comprise other accessory ingredients, such as surfactants, lubricants, disintegrants, preservatives, correctants, coloring materials, etc. On the other hand, the water-solubility of the compounds of the present invention is better than that of puerarin, thus the compounds of the present invention can readily form a preparation for systemic delivery for the prevention and treatment of cardio- and cerebrovascular diseases, diabetes and complications thereof, and chemical poisoning, in particular alcoholism.

The dosage of the compounds of the formula (I) of the present invention in tablets, capsules, coated drugs, injections and suppositories is calculated based on the amount of said compounds present in a unit dosage form. The amount of the compounds of formula (I) of the present invention in a unit dosage form is 10 to 500 mg in general, preferably 20 to 200 mg.

DESCRIPTION OF THE PREFERRED EMBODIMENTS

The present invention will be explained in detail by the following examples, but these examples are not intent to limit the protection scope of the present invention.

The instruments used in the present invention are: XY-1 Electrothermal Melting Point Meter (thermometer not calibrated) for the melting points; JNM-ECA-400 NMR Spectrometer for the NMR; and Zabspec Mass Spectrometer for MS.

Example 1

4'-(3-bromopropoxy)-7-hydroxy-8-β-D-(1-deoxyglucosyl)isoflavone ($PC_3$)

A 0.16 g (4 mmol) of sodium hydroxide was dissolved in 120 ml of anhydrous ethanol, and 0.8 g (1.92 mmol) of puerarin was added and dissolved completely by heating and refluxing. After slightly cooling, 0.20 ml (2 mmol) of 1,3-dibromopropane was added dropwisely. The reaction was continued for 5 hours under reflux. When the reaction was finished, the solvent was removed by distillation, and the resultant residue was separated by silica gel column chromatography (methylenechloride:methanol=8:1) to give 0.53 g of the title compound, yield 51.5%. mp: 196-197° C.

$^1$H NMR ($d^6$DMSO) δ(ppm): 8.39 (1H, s, $C_2$—H), 7.95 (1H, d, J=8.7, $C_5$—H), 7.52 (2H, d, J=6, $C_{2',5'}$—H), 7.01 (2H, d, J=6, $C_{3',6'}$—H), 6.99 (1H, d, J=10, $C_{1''}$-H), 4.00 (2H, t-OCH$_2$—), 3.69 (2H, q, —CH$_2$Br), 2.28 (2H, m, —CH$_2$—).

Example 2

4'-(4-bromobutoxy)-7-hydroxy-8-β-D-(1-deoxyglucosyl)isoflavone ($PC_4$)

A 0.16 g (4 mmol) of sodium hydroxide was dissolved in 120 ml of anhydrous ethanol, and 0.8 g (1.92 mmol) of puerarin was added and dissolved completely by heating and refluxing. After slightly cooling, 0.25 ml (2 mmol) of 1,4-dibromobutane was added dropwisely. And the reaction was continued for 5 hours under reflux. When the reaction was finished, the solvent was removed by distillation, and the resultant residue was separated by silica gel column chromatography (methylenechloride:methanol=8:1) to give 0.53 g of the title compound in the form of a white solid, yield 47.2%. mp: 198° C.

FAB-MS, m/z (%): 552.1 ($M^+$+1.22).

$^1$H-NMR ($d^6$DMSO) δ(ppm): 8.36 (1H, s, $C_2$—H), 7.96 (1H, d, J=9, $C_5$—H), 7.52 (2H, d, J=9, $C_{2',5'}$—H), 7.01 (2H, d, J=9, $C_{3',6'}$—H), 6.99 (1H, d, J=9, $C_6$—H), 4.86 (1H, d, J=10, $C_{1''}$—H), 4.06 (3H, m, —OCH2-, $C_{3''}$—H), 3.62 (2H, t, J=7, —CH$_2$Br), 2.02 (2H, m, —CH$_2$—), 1.99 (2H, m, —CH$_2$—).

Example 3

4'-(3-N-piperidylpropoxy)-7-hydroxy-8-β-D-(1-deoxyglucosyl)isoflavone

A 150 mg (0.27 mmol) of $PC_3$ was dissolved in 15 ml of anhydrous ethanol, 0.13 ml (1 mmol) of piperidine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 80 mg of the title compound in the form of white solid, yield 52.9%. mp: 203-205° C.

FAB-MS, m/z (%): 542 ($M^+$, 100).

$^1$H-NMR ($d^6$DMSO) δ(ppm): 8.31 (1H, s, $C_2$—H), 7.91 (1H, d, J=9, $C_5$—H), 7.51 (2H, d, J=9, $C_{2',6'}$—H), 6.97 (3H, q, J=9, $C_{3',5'}$—H, $C_6$—H). 4.83 (1H, d, J=10, $C_{1''}$—H), 4.01 (3H, m$C_{3''}$—H, —OCH$_2$—), 1.84 (2H, m, —CH$_2$—), 1.51 (4H, Hexahydropyridine$C_{3,5}$—H), 1.47 (2H, Hexahydropyridine$C_4$—H).

Example 4

4'-(3-N-morpholinylpropoxy)-7-hydroxy-8-β-D-(1-deoxyglucosyl)isoflavone

A 150 mg (0.27 mmol) of $PC_3$ was dissolved in 15 ml of anhydrous ethanol, 0.10 ml (1 mmol) of morpholine was added under stirring, and then was heated and refluxed for 9 hours. When the reaction was finished, the solvent and the excessive amine were removed by vacuum distillation. The obtained product was separated by silica gel chromatography (methanol) and then was dissolved by an eluent (methylenechloride:methanol=6:1), and the silica gel was removed by filtration to give 80 mg of the title compound in the form of a white solid, yield 52.7%. mp: 189-190° C.

FAB-MS, m/z (%): 544.1 ($M^+$, 55).

$^1$H-NMR ($d^6$DMSO) δ(ppm): 8.35 (1H, s, $C_2$—H), 7.95 (1Hd, J=9, $C_5$—H), 7.51 (2H, dJ=9, $C_{2',6'}$—H), 7.00 (3H, dd, J=9, $C_{3',5'}$—H$C_6$—H). 4.85 (1H, d, J=10, $C_{1''}$—H), 4.06 (3H, m, $C_{3''}$—H, —OCH$_2$—), 3.62 (4H, t, Morpholine$C_{2,6}$—H), 2.48 (5H, m, —CH$_2$N—, Morpholine $C_{3,5}$—H), 2.0 (2H, p, —CH$_2$—).

Example 5

4'-(3-N-pyrrolidinylpropoxy)-7-hydroxy-8-β-D-(1-deoxyglucosyl)isoflavone

A 150 mg (0.27 mmol) of $PC_3$ was dissolved in 15 ml of anhydrous ethanol, 0.13 ml (1 mmol) of pyrrolidine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 90 mg of the title compound in the form of white solid, yield 61.1%.

mp: 193-195° C.

FAB-MS, m/z (%): 555 ($M^+$+22.78), 528 ($M^+$, 100).

$^1$H-NMR ($d^6$DMSO) δ(ppm): 8.26 (1H, s, $C_2$—H), 7.82 (1H, d, J=9, $C_5$—H), 7.50 (2H, d, J=9, $C_{2',6'}$—H), 6.96 (2H, d, J=9, $C_{3',5'}$—H), 6.95 (1H, d, J=9, $C_6$—H). 4.77 (1H, d, J=10, $C_{1''}$—H), 4.00 (3H, m, $C_{3''}$—H, —$OCH_2$—), 2.50 (4H, m, Pyrrolidine $C_{2,5}$—H), 1.89 (2H, m, —$CH_2$) 1.68 (4H, m, Pyrrolidine $C_{3,4}$—H).

Example 6

4'-(3-N-diethylaminopropoxy)-7-hydroxy-8-β-D-(1-deoxyglucosyl)-isoflavone

A 150 mg (0.27 mmol) of $PC_3$ was dissolved in 15 ml of anhydrous ethanol, 0.10 ml (1 mmol) of diethylamine was added under stirring, and then the reaction was performed in an autoclave at 90° C. by heating for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 50 mg of the title compound in the form of white solid, yield 33.8%. mp: 200-203° C.

FAB-MS, m/z (%): 552 ($M^+$+22.100), 530 ($M^+$, 44).

$^1$H-NMR ($d^6$DMSO) δ(ppm): 8.24 (1H, s, $C_2$—H), 7.79 (1H, d, J=8.7, $C_5$—H), 7.50 (2H, d, J=8.7, $C_{2',6'}$—H), 6.96 (2H, d, J=8.7, $C_{3',5'}$—H), 6.76 (1H, d, J=8.7, $C_6$—H), 4.74 (1H, d, J=10$C_{1''}$—H), 4.04 (3H, m, $C_{3''}$—H, —$OCH_2$-), 2.50 (10H, m, —$(CH_2)_3$N), 1.83 (2H, m, —$CH_2$—), 0.96 (7H, q, —$CH_3$).

Example 7

4'-[3-N-di(n-propyl)aminopropoxy]-7-hydroxy-8-β-D-(1-deoxyglucosyl)-isoflavone

A 150 mg (0.27 mmol) of $PC_3$ was dissolved in 15 ml of anhydrous ethanol, 0.14 ml (1 mmol) of di(n-propyl)amine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol 6:1), and the silica gel was removed by filtration to give 40 mg of the title compound in the form of white solid, yield 25.7%.

mp: 202-205° C.

FAB-MS, m/z (%): 580 ($M^+$+22.100), 558 ($M^+$, 84).

$^1$H-NMR ($d^6$DMSO) δ(ppm): 7.90 (1H, s, $C_2$—H), 7.51 (1H, d, J=9, $C_5$—H), 7.47 (2H, d, J=8$C_{2',6'}$—H), 6.91 (2H, d, J=8, $C_{3',5'}$—H, $C_6$—H), 6.25 (1H, d, J=9, $C_6$—H), 4.57 (1H, d, J=10, $C_{1''}$—H), 4.03 (3H, m, $C_{3''}$—H, —$OCH_2$—), 2.50 (4H, m, —$N(CH_2)_2$), 1.83 (2H, m, —$CH_2$—), 0.85 (6H, t, —$CH_3$).

Example 8

4'-[3-N-di(n-butyl)aminopropoxy]-7-hydroxy-8-β-D-(1-deoxyglucosyl)-isoflavone

A 150 mg (0.27 mmol) of $PC_3$ was dissolved in 15 ml of anhydrous ethanol, 0.14 ml (1 mmol) of di(n-butyl)amine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 90 mg of the title compound in the form of white solid, yield 55.1%.

mp: 198-199° C.

FAB-MS, m/z (%): 586 ($M^+$, 12).

$^1$HNMR ($d^6$DMSO) δ(ppm): 8.04 (1H, s, $C_2$—H), 7.59 (1H, d, J=9, $C_5$—H), 7.48 (2H, d, J=8.7, $C_{2',6'}$—H), 6.92 (2H, dJ=8.7, $C_{3',5'}$—H), 6.41 (1H, d, J=9, $C_6$—H), 4.64 (1H, d, J=9.8$C_{1''}$—H), 4.03 (3H, m, $C_{3''}$—H, —$OCH_2$—), 2.49 (4H, m, —$N(CH_2)_2$—), 1.82 (2H, m, —$CH_2$—), 1.27 (11H, m, —$N(CCH_2CH_2)_2$—), 0.86 (8H, t, —$CH_3$).

Example 9

4'-(3-N-4-methylpiperazinylpropoxy)-7-hydroxy-8-β-D-(1-deoxyglucosyl)-isoflavone A 150 mg (0.27 mmol) of $PC_3$ was dissolved in 15 ml of anhydrous ethanol, 0.12 ml (1 mmol) of 1-methylpiperazine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 100 mg of the title compound in the form of white solid, yield 64.4%.

mp: 217-219° C.

FAB-MS, m/z (%): 579 ($M^+$+22.100), 557.2 ($M^+$, 58).

$^1$H-NMR ($d^6$DMSO) δ(ppm): 8.05 (1H, s, $C_2$—H), 7.66 (1H, d, J=9, $C_5$—H), 7.48 (2H, d, J=8, $C_{2',6'}$—H), 6.94 (2H, d, J=8, $C_{3',5'}$—H), 6.50 (1H, d, J=9, $C_6$—H). 4.69 (1H, d, J=10, $C_{1''}$—H), 4.03 (3H, m, $C_{3''}$—H, —$OCH_2$—), 2.49 (7H, m, —$CH_2N(CH_2)_2$—), 2.14 (3H, s, —$NCH_3$—), 1.07 (2H, p, —$CH_2$—).

Example 10

4'-(3-N-ethylpiperazinylpropoxy)-7-hydroxy-8-β-D-(1-deoxyglucosyl)-isoflavone

A 150 mg (0.27 mmol) of $PC_3$ was dissolved in 15 ml of anhydrous ethanol, 0.12 ml (1 mmol) of 1-ethylpiperazine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 110 mg of the title compound in the form of white solid, yield 69.1%. mp: 225-226° C.

FAB-MS, m/z (%): 593 ($M^+$+22.80), 571 ($M^+$, 22).

$^1$H-NMR ($d^6$DMSO) δ(ppm): 7.97 (1H, s, $C_2$—H), 7.58 (1H, d, J=9, $C_5$—H), 7.48 (2H, d, J=9, $C_{2',6'}$—H), 6.92 (2H, d, J=9, $C_{3',5'}$—H), 6.36 (1H, d, J=9, $C_6$—H), 4.64 (1H, d, J=10, $C_{1''}$—H), 4.03 (3H, m, $C_3''$-H, —$OCH_2$—), 1.88 (2H, p, —$CH_2$—), 0.98 (3H, t, —$NCH_3$).

Example 11

4'-(4-N-piperidylbutoxy)-7-hydroxy-8-β-D-(1-deoxyglucosyl)isoflavone

A 150 mg (0.27 mmol) of $PC_4$ was dissolved in 15 ml of anhydrous ethanol, 0.13 ml (1 mmol) of piperidine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 100 mg of the title compound in the form of white solid, yield 66.2%. mp: 204-205° C.

FAB-MS, m/z (%): 556 ($M^+$, 54).

$^1$H-NMR ($d^6$DMSO) δ(ppm): 8.36 (1H, s, $C_2$—H), 7.95 (1H, d, J=8, $C_5$—H), 7.53 (2H, d, J=8, $C_{2',5'}$—H), 7.03 (3H, t, J=8, $C_{3',5'}$—H, C6-H). 4.82 (1H, d, J=10, $C_{1''}$—H), 4.05 (3H, m, $C_{3''}$—H, —$OCH_2$—), 3.42 (2H, m, —$CH_2N$), 3.00 (4H, tt, Hexahydropyridine $C_{2,6}$—H), 1.78 (13H, m, pyridine $C_{3,4,5}$—H, —$CH_2CH_2$—).

Example 12

4'-(4-N-morpholinylbutoxy)-7-hydroxy-8-β-D-(1-deoxyglucosyl)isoflavone

A 150 mg (0.27 mmol) of $PC_4$ was dissolved in 15 ml of anhydrous ethanol, 0.10 ml (1 mmol) of morpholine was added under stirring, and then was heated and refluxed for 9 hours. When the reaction was finished, the solvent and the excessive amine were removed by vacuum distillation. The obtained product was separated by silica gel chromatography (methanol) and then was dissolved by an eluent (methylenechloride:methanol=6:1), and the silica gel was removed by filtration to give 80 mg of the title compound in the form of white solid, yield 52.8%. mp: 195-197° C.

FAB-MS, m/z (%): 558 ($M^+$, 43).

$^1$H-NMR ($d^6$DMSO) δ(ppm): 8.35 (1H, s, $C_2$—H), 7.96 (1H, d, J=9, $C_5$—H), 7.52 (2H, d, J=9, $C_{2',6'}$—H), 6.98 (3H, t, J=9, $C_{3',5'}$—H, $C_6$—H). 4.85 (1H, d, J=10, $C_{1''}$—H), 4.00 (4H, m, $C_{3''}$—H, —$OCH_2$—), 3.69 (3H, t, —$O(CH_2)_2$—), 2.81 (4H, m, —$N(CH_2)_2$—), 2.58 (3H, m, —$CH_2N$—), 1.76 (2H, m, —$CH_2$—), 1.68 (2H, m, —$CH_2$—).

Example 13

4'-(4-N-pyrrolidinylbutoxy)-7-hydroxy-8-β-D-(1-deoxyglucosyl)isoflavone

A 150 mg (0.27 mmol) of $PC_4$ was dissolved in 15 ml of anhydrous ethanol, 0.13 ml (1 mmol) of pyrrolidine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 110 mg of the title compound in the form of white solid, yield 74.7%.

mp: 198-199° C.

FAB-MS, m/z (%): 564 ($M^+$+22.42), 542 ($M^+$, 100).

$^1$H-NMR ($d^6$DMSO) δ(ppm): 8.16 (1H, s, $C_2$—H), 7.77 (1H, d, J=9, $C_5$—H), 7.50 (2H, d, J=9, $C_{2',6'}$—H), 6.95 (2H, d, J=9, $C_{3',5'}$—H), 6.70 (1H, d, J=9, $C_6$—H). 4.75 (1H, d, J=10, $C_{1''}$—H), 4.02 (3H, m, $C_{3''}$—, —$OCH_2$—), 2.49 (6H, m, —$CH_2N(CH_2)_2$—), 1.68 (9H, m, —$CH_2CH_2$—, Pyrrolidine$C_{3,4}$—H).

Example 14

4'-(4-N-diethylaminobutoxy)-7-hydroxy-8-β-D-(1-deoxyglucosyl)isoflavone

A 150 mg (0.27 mmol) of $PC_4$ was dissolved in 15 ml of anhydrous ethanol, 0.10 ml (1 mmol) of diethylamine was added under stirring, and then the reaction was performed in an autoclave at 90° C. by heating for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 60 mg of the title compound in the form of white solid, yield 40.6%. mp: 206-207° C.

FAB-MS, m/z (%): 544 ($M^+$, 18).

$^1$H-NMR ($d^6$DMSO) δ(ppm): 8.08 (1H, s, $C_2$—H), 7.62 (1H, d, J=9, $C_5$—H), 7.48 (2H, d, J=9, $C_{2',6'}$—H), 6.91 (2H, d, J=9, $C_{3',5'}$—H), 6.47 (1H, d, J=9, $C_6$—H), 4.68 (1H, d, J=10, $C_{1''}$—H), 4.01 (3H, m, $C_{3''}$—H, —$OCH_2$—), 2.41 (4H, m, —$N(CH_2)_2$—), 1.75 (2H, p, —$CH_2$—), 1.58 (2H, p, —$CH_2$—), 0.92 (6H, t, —$CH_3$).

Example 15

4'-(4-N-di(n-propyl)aminobutoxy)-7-hydroxy-8-β-D-(1-deoxyglucosyl)-isoflavone

A 150 mg (0.27 mmol) of $PC_4$ was dissolved in 15 ml of anhydrous ethanol, 0.14 ml (1 mmol) of di(n-propyl)amine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 40 mg of the title compound in the form of white solid, yield 25.7%.

mp: 199-203° C.

FAB-MS, m/z (%): 572 ($M^+$, 100).

$^1$H-NMR ($d^6$DMSO) δ(ppm): 8.39 (1H, s, $C_2$—H), 7.95 (1H, d, J=9, $C_5$—H), 7.51 (2H, d, J=8.7, $C_{2',6'}$—H), 6.99 (2H, d, J=8.7, $C_{3',5'}$—H), 6.88 (1H, d, J=9, $C_6$—H). 4.82 (1H, d, J=10, $C_{1''}$—H), 4.02 (3H, m, $C_{3''}$—H, —$OCH_2$—), 1.41-1.73 (11H, —$CH_2CH_2$—, —$N(CCH_2)_2$—), 0.86 (8H, t-$CH_3$).

Example 16

4'-(4-N-di(n-butyl)aminobutoxy)-7-hydroxy-8-β-D-(1-deoxyglucosyl)-isoflavone

A 150 mg (0.27 mmol) of $PC_4$ was dissolved in 15 ml of anhydrous ethanol, 0.14 ml (1 mmol) of di(n-butyl)amine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 100 mg of the title compound in the form of white solid, yield 61.3%.

mp: 198-200° C.

FAB-MS, m/z (%): 622 ($M^+$+22.100), 600 ($M^+$, 100).

$^1$H-NMR ($d^6$DMSO) δ(ppm): 8.10 (1H, s, $C_2$—H), 7.67 (1H, d, J=9, $C_5$—H), 7.49 (2H, d, J=9, $C_{2',6'}$—H), 6.94 (2H, d, J=9, $C_{3',5'}$—H), 6.52 (1H, d, J=9, $C_6$—H), 4.89 (1H, d, J=10, $C_{1''}$—H), 4.00 (3H, m, $C_{3''}$—H, —$OCH_2$—), 1.28 (8H, m, N($CCH_2CH_2$)$_2$—), 0.88 (6H, t, —$CH_3$).

Example 17

4'-(4-N-methylpiperazinylbutoxy)-7-hydroxy-8-β-D-(1-deoxyglucosyl)-isoflavone

A 150 mg (0.27 mmol) of $PC_4$ was dissolved in 15 ml of anhydrous ethanol, 0.12 ml (1 mmol) of 1-methylpiperazine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 110 mg of the title compound in the form of white solid, yield 70.9%.

mp: 225-228° C.

FAB-MS, m/z (%): 593 ($M^+$+22.84), 571 ($M^+$, 38).

$^1$H-NMR ($d^6$DMSO) δ(ppm): 7.99 (1H, s, $C_2$—H), 7.60 (1H, d, J=9, $C_5$—H), 7.48 (2H, d, J=9, $C_{2',6'}$—H), 6.93 (2H, d, J=9, $C_{3',5'}$—H), 6.39 (1H, d, J=9, $C_6$—H), 4.86 (1H, d, J=10, $C_{1''}$—H), 4.10 (3H, m, $C_{3''}$—H, —$OCH_2$—), 2.49 (8H, 1-Methylpiperazine $C_{2,3,5,6}$—H), 2.13 (3H, s, —$NCH_3$).

Example 18

4'-(4-N-ethylpiperazinylbutoxy)-7-hydroxy-8-β-D-(1-deoxyglucosyl)-isoflavone

A 150 mg (0.27 mmol) of $PC_4$ was dissolved in 15 ml of anhydrous ethanol, 0.13 ml (1 mmol) of 1-ethylpiperazine was added under stirring, and then was heated and refluxed for 9 hours. When the reaction was finished, the solvent and the excessive amine were removed by vacuum distillation. The obtained product was separated by silica gel chromatography (methanol:triethylamine=200:1) and then was dissolved by an eluent (methylenechloride:methanol=6:1), and the silica gel was removed by filtration to give 110 mg of the title compound in the form of white solid, yield 69.2%.

mp: 228-230° C.

FAB-MS, m/z (%): 607 ($M^+$+22.96), 585 ($M^+$, 54).

$^1$H-NMR ($d^6$DMSO) δ(ppm): 8.02 (1H, S, $C_2$—H), 7.64 (1H, d, J=9, $C_5$—H), 7.48 (2H, d, J=9, $C_{2',6'}$—H), 6.93 (2H, d, J=9, $C_{3',5'}$—H), 6.45 (1H, d, J=9, $C_6$—H), 4.68 (1H, d, J=10, $C_{1''}$—H), 4.06 (3H, m, $C_{3''}$—H, —$OCH_2$—), 2.38 (11H, t, 1-Ethylpiperazine $C_{2,3,5,6}$—H), 1.74 (2H, t, —$CH_2$—), 1.58 (2H, m, —$CH_2$), 0.99 (3H, t, —$CH_3$).

Example 19

Preparation of Hydrochlorides and Tests of Solubility

General method for preparing hydrochlorides: dissolving a compound of examples 1 to 18 in anhydrous methanol, cooling by ice-water bath, adding dropwisely a sufficient amount of an ethyl ether solution of anhydrous hydrogen chloride to complete the formation of salt, washing the formed solid with anhydrous ethyl ether until it is not acidic, and recrystallizing to obtain a solid crystal of the hydrochloride.

Semi-quantitative test of solubility: weighing 100 mg of the hydrochloride of said compound, adding it to 2 ml of distilled water, stirring at room temperature until it is dissolved completely. This indicates that the hydrochloride of said compound has a solubility of greater than 5 g/100 ml in water, which is 10 folds greater than the solubility of puerarin.

Test Example 1

In Vitro Experiment of Vessel Ring Dilatation

This test was carried out according to a conventional method well known by the person skilled in the art.

Wistar rats were sacrificed by decapitation and subjected to throcolaparotomy quickly. Aorta in thoracic and abdominal cavity was excised and placed in a culture dish containing vascular nutrition liquid. The peri-vascular tissues were removed and the aorta was cut to form strips of about 3 mm-long, and each strip was penetrated carefully with two stainless wires of diameter about 0.1 mm to form a triangular ring, then the ring was placed in a 37° C. thermostatic bath containing 10 mg of blood nutrition liquid, fixed and connected with a tension sensor and the signal thereof was further inputted into an automatic desktop balance recorder. A mixed gas of 95% $O_2$ and 5% was ventilated. After being stabilized, the drugs were screened. Noradrenaline was added to reach the maximum of vasoconstriction balance, and then 0.1 ml of a solution of a drug-candidate was added to the bath, to a concentration of $10^{-5}$M, and was observed for 10 minutes. After changing the liquids, noradrenaline was added to reach the maximal vasoconstriction, and the integrality of blood vessel endothelium was verified by $10^{-6}$M of Ach. measuring the recordation diagram to obtain the maximum vasoconstriction Measuring of the maximal contraction rate and the contraction rate after administration, and the vasodilatation rates were calculated therefrom.

Test Example 2

Normal Pressure Hypoxia-Resistance Test in Mice

This test was carried out by a common method familiar to those skilled in the art. 32 Kunming mice (16 males vs. 16 females, body weights ranging from 18 to 20 g) were randomly divided into a control group and a administration group (each group having 16 animals), wherein the dosage was 60 mg/Kg mouse and 0.2 ml for each animal. After 0.5 hours of the intraperitoneal injection of test solutions, the mice were placed and sealed in 250 ml wide-mouthed bottles with ground stoppers. The times of death were recorded. Statistical analysis was conducted separately with respect to the blank control group and puerarin group, and P values were calculated.

TABLE

Results of hypoxia-resistant activities

| Compounds of examples | Time to death (min) | $P_1$ (blank) | $P_2$ (puerarin) |
| --- | --- | --- | --- |
| Physiological saline | 37.5 ± 4 | | |
| Physiological saline + CMC | 37.8 ± 5 | | |
| Physiological saline + CMC + puerarin | 48.3 ± 5 | | |
| Example 4 | 75.3 ± 7 | <0.05 | <0.05 |
| Example 6 | 73.5 ± 9 | <0.05 | <0.05 |
| Example 7 | 69.8 ± 5 | <0.05 | <0.05 |
| Example 14 | 79.1 ± 8 | <0.05 | <0.05 |
| Example 17 | 59.8 ± 7 | <0.05 | >0.05 |
| Example 18 | 75.9 ± 6 | <0.05 | <0.05 |

※ represents that the mouse died during the standing after it was administered; and "P < 0.05" means that the time of death of the mice were significantly prolonged by the compound in comparison with the blank group and puerarin group. The compounds in the Table are corresponding hydrochloride salts of the compounds prepared in the examples.

According to the above test results, the person skilled in the art can well understand that the compounds of the present invention have effects of vasodilatation and hypoxia-resistance effects on mammals.

Test Example 3

Hypoglycemic Test of Diabetic Rats

Male Wistar rats with body weights ranging from 150 to 180 g were randomly divided into groups, and were induced to form diabetic model rats by intraperitoneal injection of streptozotocin (STZ, SIGMA, dissolved in 0.1 molL$^{-1}$ citrate buffer, pH=4.5) in a single dosage of 65 mgKg$^{-1}$. The administration groups were intraperitoneally injected daily with a dosage of 80 mgKg$^{-1}$, while the blank control group was intraperitoneally injected with physiological saline in an equivalent volume. Animals took food and drank water freely for 16 weeks. The blood sugar and the expression of matrix metalloproteinase 3 (MMP-3) and tissue inhibitor of metalloproteinase 1 (TIMP-1) were assayed. The results show that these compounds can effectively reduce the blood sugar level, and exhibit protection effects on renal function and morphology of diabetic rats.

Test Example 4

Measurement of Ethanol Content in Blood of Rats of Acute Alcoholism

SD rats (weight ranging from 180 to 240 g, half male and half female) were randomly divided into groups, and were intragastrically administered with 40% ethanol in a dosage of 5.5 g·Kg$^{-1}$, wherein the rats of the administration group intragastrically administered with a drug simultaneously, while the rats of the control group were administrated with physiological saline. The post-eyeball venous plexus blood was collected separately after 15, 30, 45, 60, 90 and 120 minutes of the intragastric administration. The blood serum was obtained by centrifugation and was analyzed by directly loading in a gas chromatography to determine the changes of ethanol concentrations in blood samples. The results show that these compounds can effectively reduce the ethanol concentration in blood of rats of acute alcoholism.

The present invention is promising in the manufacture of medicaments for the treatment of cardio- and cerebrovascular diseases in mammalians including human, particularly medicaments for the treatment of hypoxia and ischemia. The present invention has potential value in the manufacture of medicaments for the treatment of diabetes and complications thereof, and medicaments for the treatment of chemical poisoning, particularly alcoholism.

What is claimed is:

1. A C-Glycosylisoflavone compound of the formula (I) having alkylaminoalkoxyl substituent or a pharmaceutically acceptable salt thereof:

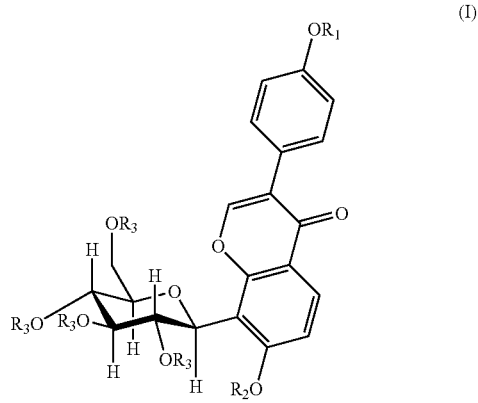

wherein, $R_1$ and $R_2$ are independently selected from the group consisting of hydrogen, ($C_1$-$C_{12}$) linear or branched alkylamino ($C_1$-$C_6$)alkyl, mono- or di-($C_{3-8}$)cycloalkylamino-$C_{1-6}$alkyl, and ($C_5$-$C_{14}$)heterocyclic-($C_1$-$C_6$)alkyl; $R_3$ is selected from the group consisting of hydrogen, ($C_1$-$C_{12}$) linear or branched acyl and $C_{6-14}$ aryl carbonyl; wherein $R_1$ and $R_2$ do not represent hydrogen simultaneously; the 1-position of D-glucosyl is connected with the 8-position of the isoflavone in a form of β-configured C-glycoside, wherein the mono- or di-($C_{3-8}$) cycloalkylamino group of the mono- or di-($C_{3-8}$) cycloalkylamino-$C_{1-6}$alkyl includes pyrrolidinyl and morpholinyl, and the ($C_5$-$C_{14}$)heterocyclic group of the ($C_5$-$C_{14}$) heterocyclic-($C_1$-$C_6$)alkyl is selected from the group consisting of piperidyl, piperazinyl, N-methylpiperazinyl, and N-ethylpiperazinyl.

2. The compound according to claim 1, characterized in that in formula (I), $R_1$ and $R_2$ are independently selected from the group consisting of hydrogen, dimethylaminoethyl, diethylaminoethyl, di(n-propyl)aminoethyl, di(iso-propyl) aminoethyl, di(n-butyl)aminoethyl, di(iso-butyl)aminoethyl, di(tert-butyl)aminoethyl, pyrrolidinylethyl, piperidylethyl, morpholinylethyl, piperazinylethyl, N-methylpiperazinylethyl, N-ethylpiperazinylethyl, tert-butylaminoethyl, dicyclohexylaminoethyl, dimethylaminopropyl, diethylaminopropyl, di(n-propyl)aminopropyl, di(iso-propyl)aminopropyl, di(n-butyl)aminopropyl, di(iso-butyl)aminopropyl, di(tert-butyl)aminopropyl, pyrrolidinyipropyl, piperidyipropyl, morpholinylpropyl, piperazinylpropyl, N-methylpiperazinylpropyl, N-ethylpiperazinylpropyl, tert-butylaminopropyl, dicyclohexylaminopropyl, dimethylaminobutyl, diethylaminobutyl, di(n-propyl)aminobutyl, di(iso-propyl)aminobutyl, di(n-butyl)aminobutyl, di(iso-butyl)aminobutyl, di(tert-butyl)aminobutyl, pyrrolidinylbutyl, piperidylbutyl, morpholinylbutyl, piperazinylbutyl, N-methylpiperazinylbutyl, N-ethylpiperazinylbutyl, tert-butylaminobutyl and dicyclohexylaminobutyl, wherein $R_1$ and $R_2$ do not represent hydrogen simultaneously; $R_3$ is selected from the group consisting of hydrogen, propionyl, butyryl, isobutyryl, 2-methylbutyryl, 3-methylbutyryl, 2,2-dimethylpropionyl, valeryl, caproyl, heptanoyl, octanoyl, nonanoyl, decanoyl, and lauroyl; and wherein the pharmaceutically acceptable salt is selected from the group consisting of salts of hydrochloric acid, hydrobromic acid, phosphoric acid, phosphorous acid, sulfuric acid, methane sulfonic acid, p-toluene sulfonic acid, maleic acid, fumaric acid, tartaric acid, and various natural or non-natural amino acids.

3. The compound according to claim 1, wherein the compound of the formula (I) is selected from the group consisting of:

4'-(3-N-piperidylpropoxy)-7-hydroxy-8-β-D-(1-deoxyglucosyl)isoflavone,

4'-(3-N-morpholinylpropoxy)-7-hydroxy-8-β-D-(1-deoxyglucosyl)isoflavone,

4'-(3-N-pyrrolidinylpropoxy)-7-hydroxy-8-β-D-(1-deoxyglucosyl)isoflavone,

4'-(3-diethylaminopropoxy)-7-hydroxy-8-β-D-(1-deoxyglucosyl)isoflavone,

4'-[3-di(n-propyl)aminopropoxy]-7-hydroxy-8-β-D-(1-deoxyglucosyl) isoflavone,

4'-[3-di(n-butyl)aminopropoxy]-7-hydroxy-8-β-D-(1-deoxyglucosyl) isoflavone,

4'-[3-(4-methylpiperazinyl)propoxy]-7-hydroxy-8-β-D-(1-deoxyglucosyl) isoflavone, 4'-[3-(4-ethylpiperazinyl)propoxy]-7-hydroxy-8-β-D-(1-deoxyglucosyl) isoflavone, 4'-(4-N-piperidylbutoxy)-7-hydroxy-8-β-D-(1-deoxyglucosyl)isoflavone, 4'-(4-N-morpholinylbutoxy)-7-hydroxy-8-β-D-(1-deoxyglucosyl)isoflavone, 4'-(4-N-pyrrolidinylbutoxy)-7-hydroxy-8-β-D-(1-deoxyglucosyl)isoflavone, 4'-(4-diethylaminobutoxy)-7-hydroxy-8-β-D-(1-deoxyglucosyl)isoflavone, 4'-(4-di(n-propyl)aminobutoxy)-7-hydroxy-8-β-D-(1-deoxyglucosyl)-isoflavone, 4'-(4-di(n-butyl)aminobutoxy)-7-hydroxy-8-β-D-(1-deoxyglucosyl) isoflavone, 4'-[4-(4-methylpiperazinyl)butoxy]-7-hydroxy-8-β-D-(1-deoxyglucosyl) isoflavone, 4'-[4-(4-ethylpiperazinyl)butoxy]-7-hydroxy-8-β-D-(1-deoxyglucosyl) isoflavone, and a pharmaceutically acceptable salt thereof.

4. A pharmaceutical composition comprising the C-Glycosylisoflavone compound of claim 1 and a pharmaceutically acceptable carrier.

5. A preparation method of the C-Glycosylisoflavone compound of claim 1, characterized in comprising, reacting puerarin material with a corresponding bis-functional group substituted compound, in a suitable solvent selected from water, acetone, dimethylformamide, dimethyl sulfoxide, and lower alcohols, under the presence of a base, an ambient to reflux-temperature, which is firstly mono-etherified followed by amination and/or salt-formation, to give the corresponding alkylaminoalkoxyl-substituted C-Glycosylisoflavone compound or a pharmaceutically acceptable salt thereof.

6. A method for treatment of cardio- and cerebrovascular diseases as well as hypoxia or ischemia, comprising administering a therapeutically effective amount of the C-Glycosylisoflavone compound of claim 1 to a patient in need.

7. A method for treatment of diabetes as well as diabetic complications, comprising administering a therapeutically effective amount of the C-Glycosylisoflavone compound of claim 1 to a patient in need.

8. A method for treatment of chemical poisoning, comprising administering a therapeutically effective amount of the C-Glycosylisoflavone compound of claim 1 to a patient in need.

9. The preparation method as set forth in claim 5, wherein said bis-functional group substituted compound is selected from the group consisting of a bihalogenated hydrocarbon, an alkylene bissulfonate, and a halogenated hydrocarbon monosulfonate.

10. The method as set forth in claim 8, wherein said chemical poisoning is alcohol poisoning.

* * * * *

UNITED STATES PATENT AND TRADEMARK OFFICE
CERTIFICATE OF CORRECTION

PATENT NO. : 7,727,965 B2
APPLICATION NO. : 10/563471
DATED : June 1, 2010
INVENTOR(S) : Lin Wang et al.

Page 1 of 1

It is certified that error appears in the above-identified patent and that said Letters Patent is hereby corrected as shown below:

| | |
|---|---|
| Column 15, Claim 2, line 6 | Delete "pyrrolidinyipropyl" <br> Insert -- pyrrolidinylpropyl -- |
| Column 15, Claim 2, line 7 | Delete "piperidyipropyl" <br> Insert -- piperidylpropyl -- |

Signed and Sealed this
Thirty-first Day of May, 2011

David J. Kappos
*Director of the United States Patent and Trademark Office*